United States Patent [19]
Gaba

[11] Patent Number: 5,584,809
[45] Date of Patent: Dec. 17, 1996

[54] SAFETY CATHETER

[75] Inventor: Rodolfo Gaba, Simi Valley, Calif.

[73] Assignee: Graphic Controls Corporation, Buffalo, N.Y.

[21] Appl. No.: 472,553

[22] Filed: Jun. 7, 1995

Related U.S. Application Data

[63] Continuation-in-part of Ser. No. 376,399, Jan. 23, 1995, Pat. No. 5,533,974, which is a continuation-in-part of Ser. No. 94,842, Jul. 20, 1993, Pat. No. 5,417,659.

[51] Int. Cl.[6] .................................................... A61M 5/00
[52] U.S. Cl. ........................................ 604/110; 604/192
[58] Field of Search ................................... 604/110, 164, 604/165, 198, 263, 192, 900

[56] References Cited

U.S. PATENT DOCUMENTS

| | | | |
|---|---|---|---|
| Re. 34,416 | 10/1993 | Lemieux | 604/164 |
| 4,728,321 | 3/1988 | Chen | 604/110 |
| 4,747,831 | 5/1988 | Kulli | 604/110 |
| 4,798,587 | 1/1989 | Willoughby | 604/110 |
| 4,986,811 | 1/1991 | Thead et al. | 605/110 |
| 4,995,871 | 2/1991 | Sasaki et al. | 604/110 |
| 5,187,850 | 2/1993 | McCammon et al. | 29/235 |
| 5,195,983 | 3/1993 | Boese | 604/110 X |
| 5,279,581 | 1/1994 | Firth et al. | 604/193 |
| 5,322,517 | 6/1994 | Sircom et al. | 604/198 |
| 5,328,482 | 7/1994 | Sircom et al. | 604/198 |
| 5,334,158 | 8/1994 | McLees | 604/110 |
| 5,411,486 | 5/1995 | Zadini et al. | 604/165 X |
| 5,417,659 | 5/1995 | Gaba | 604/110 |

*Primary Examiner*—John D. Yasko
*Attorney, Agent, or Firm*—Lyon & Lyon

[57] ABSTRACT

A safety catheter has a needle extending from a needle assembly. A needle point lock has a housing, a locking arm with a hook extending outside of the housing and a rear tab. A wheel within the housing is pushed against a ramp surface and the rear tab of the locking arm, by a spring. The needle extends through the housing and a hole or slot in the locking arm, and into the catheter. The hub of the catheter is held against the housing by the hook on the locking arm, until the needle is withdrawn into the housing, releasing the locking arm and allowing the hook to separate from the catheter hub. After the point of the needle has been withdrawn into the housing, it cannot be pushed back out as the needle slot moves out of alignment with the needle point. The needle also cannot be withdrawn from the back of the housing as the tab on the locking arm moves to allow the wheel to engage the needle with a wedging action. The catheter cannot be accessed until the needle point is withdrawn and safely locked within the housing.

19 Claims, 4 Drawing Sheets

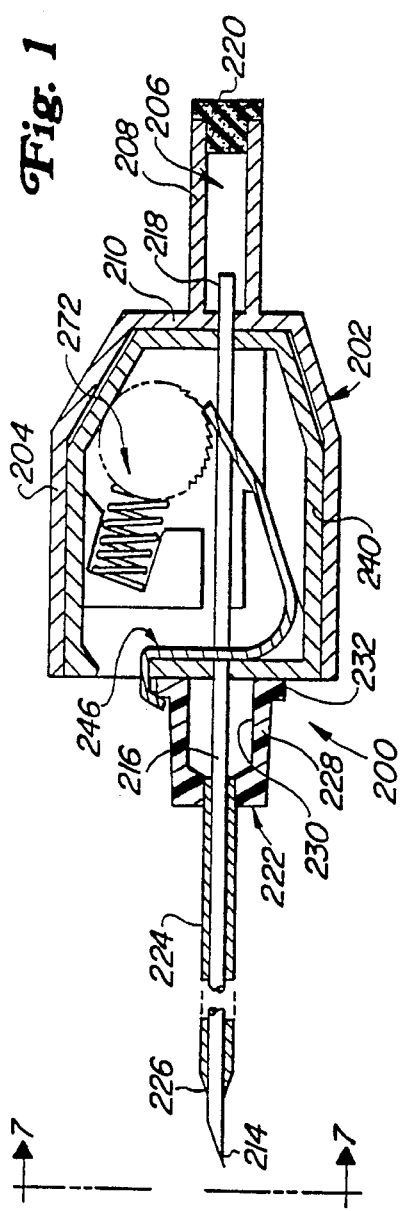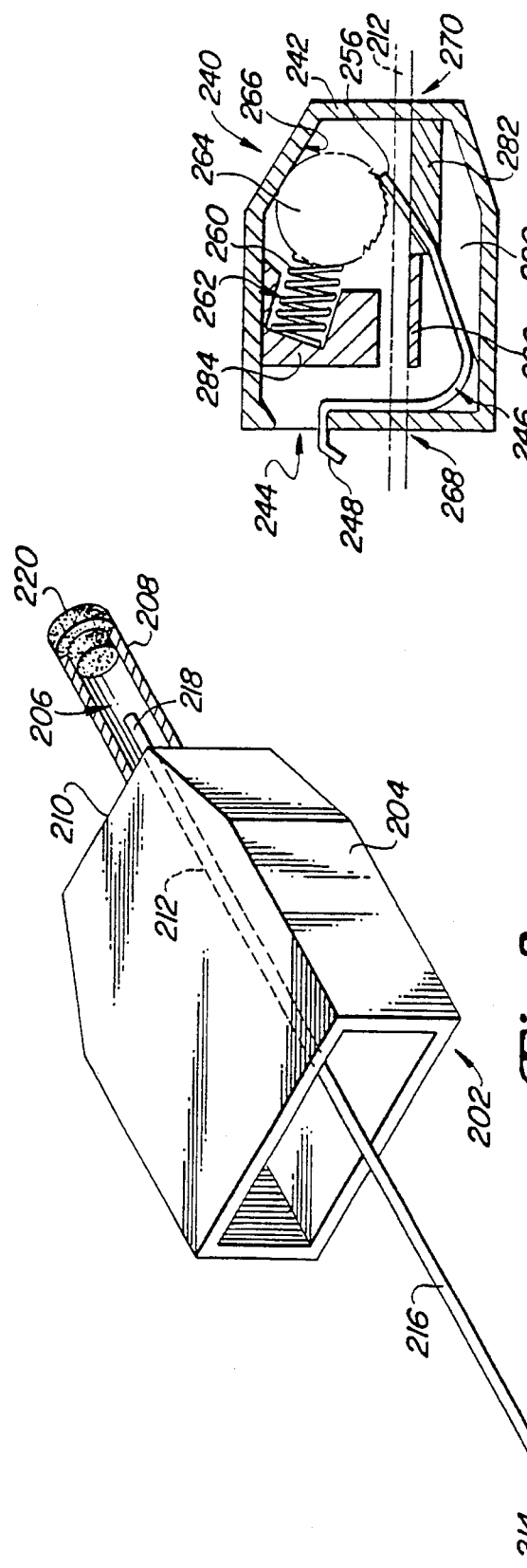

5,584,809

SAFETY CATHETER

This application is a continuation-in-part of Ser. No. 08/376,399, filed Jan. 23, 1995, incorporated herein by reference and now U.S. Pat. No. 5,533,974 which in turn is a continuation-in-part of Ser. No. 08/094,842, filed Jul. 20, 1993, and now U.S. Pat. No. 5,417,659.

BACKGROUND OF THE INVENTION

The invention relates to safety catheters. Catheters (i.e., a small tube or needle typically inserted into a vein) are widely used in hospitals to intravenously provide fluids such as blood, plasma, medication, etc. A catheter typically allows a number of intravenous (IV) tubes to be interchangeably connected, and is often left in a patient's arm even when not used, so that additional punctures need not be made for subsequent IV tubes or applications.

Catheters are inserted into the patient with a large-bore stylette or needle. In the most common configuration, the catheter is sold in a sterile pack with the catheter surrounding the needle. A removable plastic needle cover or cap may also be provided around the catheter and needle. In use, the plastic needle cover is first removed, the needle is used to puncture the patient's skin, and the needle and associated catheter are pushed into the puncture. The needle is then withdrawn from the patient and temporarily placed nearby while the catheter is held in place within the puncture site. Then, the catheter is taped to the patient and connected to the infusion set or other lines.

The need to immediately tape and connect an IV catheter generally takes priority over safe needle handling and disposal. The used needle may then be inadvertently left uncapped on a tray, bedsheet, cart, etc. Such a loose sharp instrument creates a significant safety risk to patients and medical personnel. Various types of so-called safety IV catheters have been previously provided to counter this problem. These devices usually include mechanisms designed to prevent needlesticks. However, conventional safety IV catheters tend to be bulky, difficult to use, and/or expensive. In addition, if not used correctly, their safety features can be inadvertently bypassed.

Accordingly, a need exists for an improved catheter which can be safely, quickly and reliably used and disposed of after use.

SUMMARY OF THE INVENTION

To these ends, a safety IV catheter most desirably includes a point lock for covering the point of a sharp, i.e., a needle, trocar, scalpel, etc. The point lock preferably includes a housing, a wheel and a wedge surface. Once locked, the point lock prevents the sharp from being withdrawn from the housing. The instrument point or edge is therefore safely and virtually permanently contained within the housing. In a preferred embodiment, a locking arm is provided to prevent separation of the catheter from the point lock.

BRIEF DESCRIPTION OF THE DRAWING

In the drawings, wherein similar reference characters denote similar elements, throughout the several views.

FIG. 1 is a longitudinal section view of the present catheter;

FIG. 2 is a perspective view of the needle assembly of the catheter of FIG. 1;

FIG. 3 is a section view of the needle point lock of the catheter of FIG. 1;

DETAILED DESCRIPTION OF THE DRAWINGS

Figure 4:
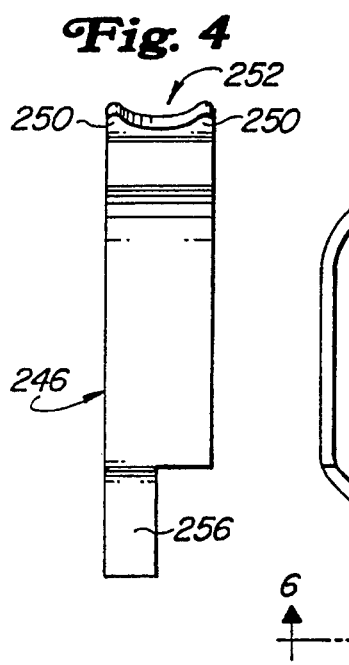
FIG. 4 is a front elevation view of the locking arm of the catheter of FIG. 1.

Referring now in detail to the drawings, as shown in FIG. 1, the present safety catheter 200 includes a needle assembly 202, a needle point lock 240 and a catheter 222. As shown in FIG. 2, the needle assembly 202 has a housing cover 204 forming an open interior space, to receive the needle point lock 240. A preferably clear tube 208 extends from the back wall 210 of the housing cover 204, and is capped off with a vent 220 made of an air porous material. The tube 208 forms a cylindrical flash back chamber 206. The bore 215 at the back end 218 of a needle 212 opens into the flash back chamber 206. The needle passes through and is held in position by the back wall 210, extends forward through and projects substantially beyond the housing cover 204, to a point 214. The length of the shaft 216 of the needle 212 is selected to cooperate with the catheter 222 used and the particular medical application of the safety catheter unit 200.

Figure 7:
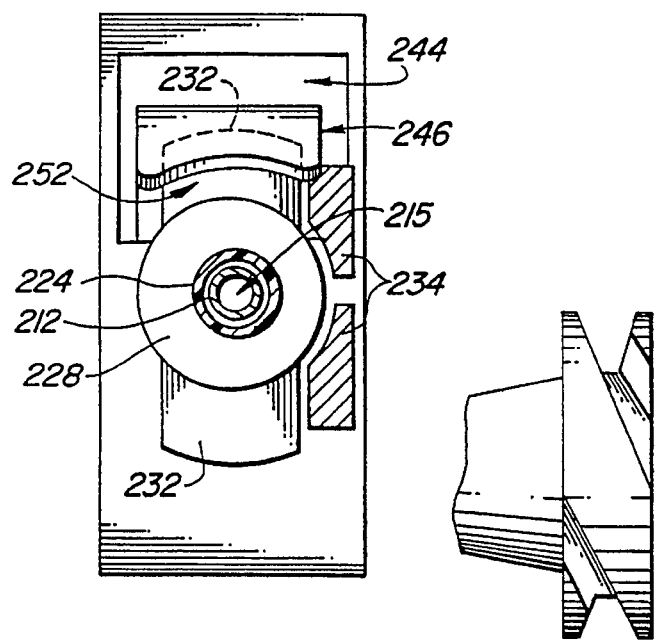
FIG. 7 is a front elevation view of the catheter of FIG. 1.
Figures 7A, 7B:
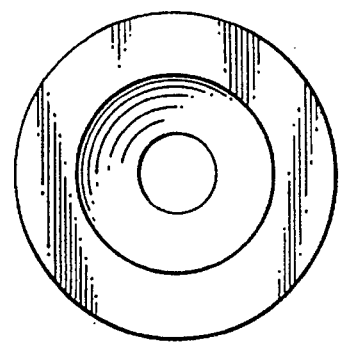
FIG. 7A is a rear end view of a full ring luer lock on a standard catheter.
FIG. 7B is a partial side elevation view thereof.

Referring once again to FIG. 1, the catheter 222 has a point 226, on a catheter shaft 224, having a hub 228 at the back end. The interior of the hub 228 has a fitting 230, such as a Luer fitting, adapted to connect with intravenous or other tubes or fittings. As shown in FIG. 7, the hub 228 of the catheter 222 includes luer lock flanges 232, but may otherwise preferably be a full ring luer lock 299 as seen in standard catheters.

Referring to FIG. 3, the needle point lock 240 has a housing enclosing a locking mechanism 272. The housing has a floor 280 and continuous walls, and a cover (not shown). A front opening 244 is provided in the flat front wall of the housing. A front needle hole 268 passes through the front wall of the housing 242, below the front opening 244, and is aligned with a rear needle hole 270 in the rear wall of the housing 242.

A spring block 284, a guide 286, and a shelf 282 are attached to or integral with the floor 280 and/or walls of the housing 242. The shelf 282 has a height which is only a fraction of the height of the housing 242, while the spring lock 284 and guide 286 preferably extend entirely from the floor 280 to the cover.

Figure 5:
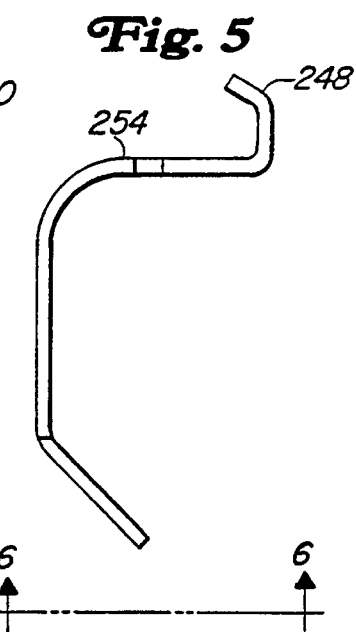
FIG. 5 is a side elevation view thereof.
Figure 6:
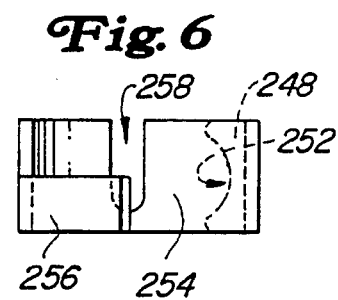
FIG. 6 is a rear elevation view thereof.

As shown in FIGS. 4, 5 and 6, a locking arm 246 has a hook 248 formed by prongs 250 on opposite sides of a cut out 252. The locking arm 246 is positioned within the housing 242 with a tab 256 on the locking arm 246 extending over the shelf 282. A needle slot or hole 258 is provided in the front leg 254 of the locking arm 246.

Referring to FIGS. 1 and 3, a spring 260 positioned within a spring bore 262 extends to push against a wheel 264, urging the wheel 264 against a ramp 266 on the housing 242, and against the tab 256 on the back end of the locking arm 246. The wheel 264 has a toothed, knurled, roughened or other engagement/friction surface.

Referring to FIG. 1, with the safety catheter 200 assembled and ready for use (e.g., as it would be provided in a sterile package), the housing cover 204 of the needle assembly 202 is positioned over and around the housing 242 of the needle point lock 240, with the needle 212 of the needle assembly 202 extending through the rear needle hole 270, through the needle slot 258 in the locking arm 246, through the front needle hole 268, and into and through the catheter 222. The diameter of the needle 212 is selected to fit closely within the catheter shaft 224, and the length of the needle 212 allows the point 214 to project just beyond the point 226 of the catheter shaft 224, as shown in FIG. 1. With the needle 212 extending through the needle slot 258, the hook 248 on the locking arm 246 is held down, clamping the rear flat surface of the hub 228 of the catheter 222 against the front flat surface of the housing 242. Referring momentarily to FIG. 7, flange stops 234 on the front surface of the housing 242 prevent rotation of the catheter 222, so that the flanges 232 on the hub 228 of the catheter cannot rotate or move out from under the hook 248 of the locking arm 246. If a full ring 299 luer lock is used, flanges 232 are not needed as catheter rotation will not affect its retention by hook 248 of locking arm 246.

Figure 8:
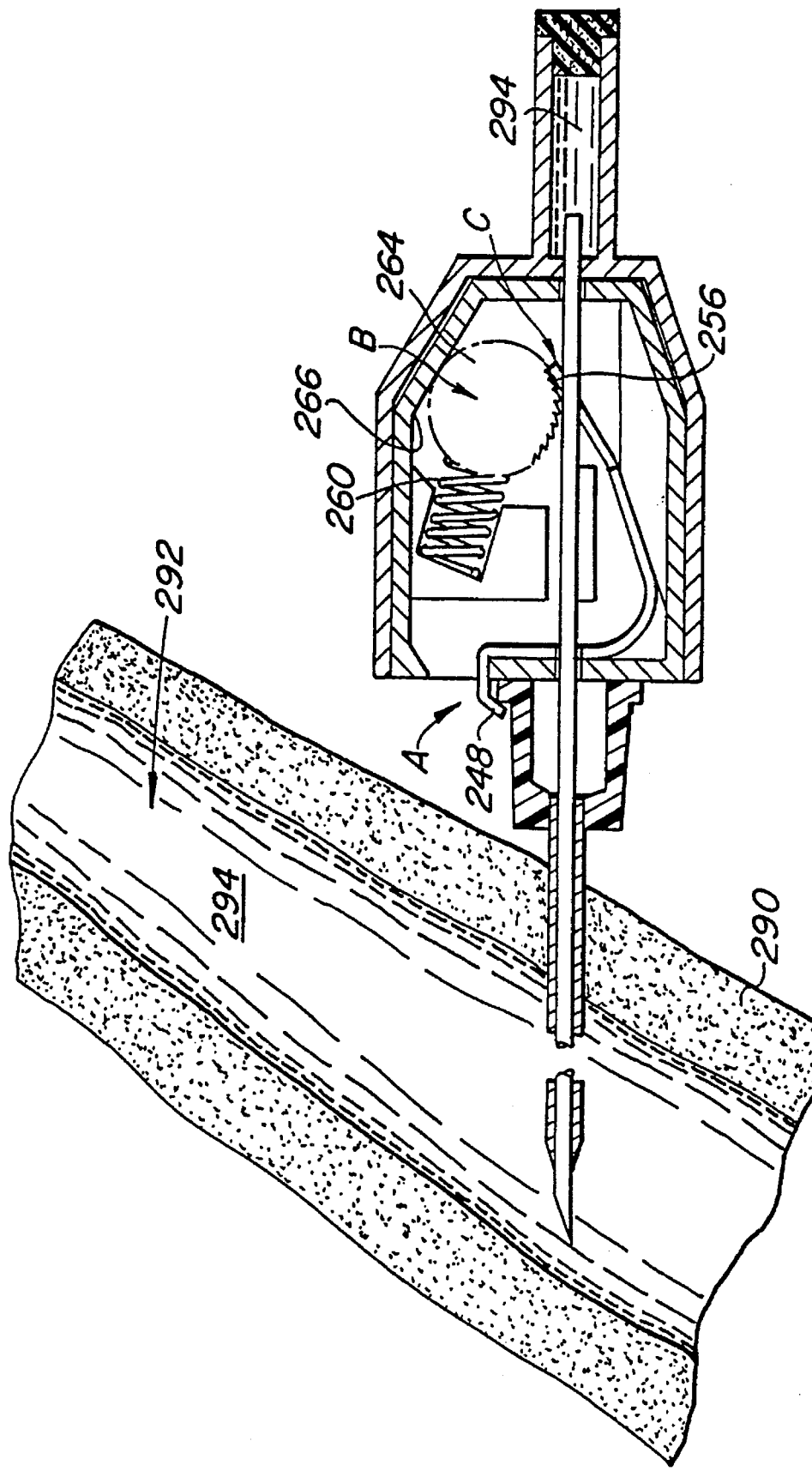
FIG. 8 is a side section view of the catheter of FIG. 1 in use, inserted into a blood vessel.

In typical use, as shown in FIG. 8, the safety catheter 200 as it is shown in FIG. 1, is removed from its package. The needle 212, along with the catheter shaft 224 is pushed through the skin and tissue 290 into a blood vessel 292. Blood 294 flows through the hollow needle 212 into the flash back chamber 206. Air in the flash back chamber 206 is displaced by the blood 294 and diffuses out through the vent 220, which allows air, but not blood to pass through. The presence of blood 294 in the flash back chamber 206 provides a visual indication to the user.

Figure 9:
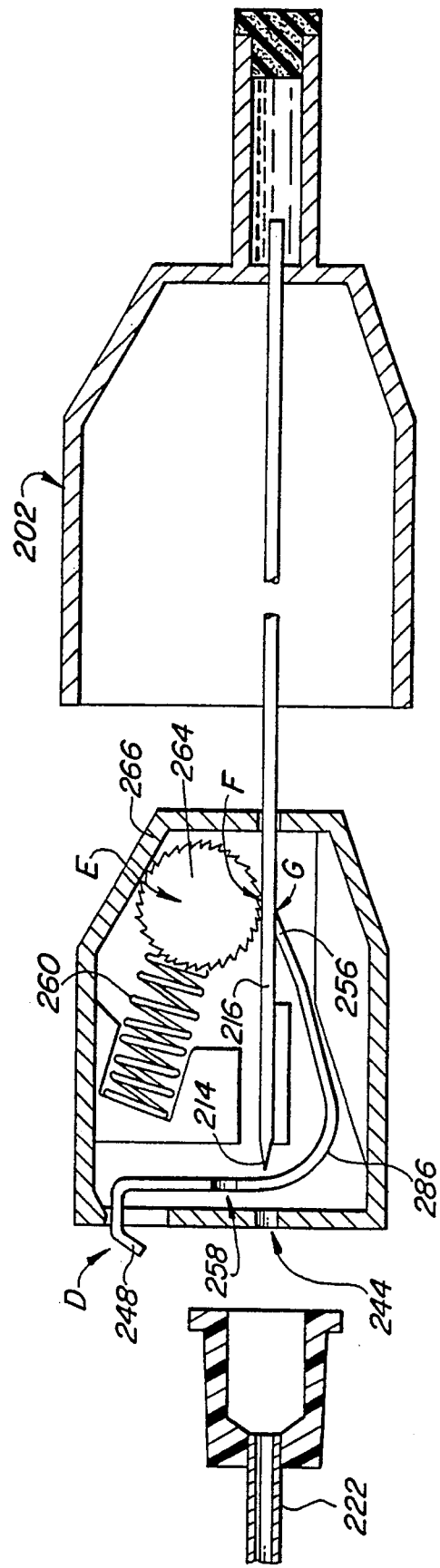
FIG. 9 is a side section view illustrating the locking features of the catheter of FIG. 1.

Referring to FIGS. 8 and 9, while the catheter 222 is held in position, the needle assembly 202 is pulled back and separates from the needle point lock 240. The locking arm 246, in position A, keeps the needle point lock 240 attached to the catheter 222. The tab 256, in position C, holds the wheel 264, in position B, away from the needle. When the needle assembly 212 is pulled back sufficiently, the point 214 of the needle 212 is pulled within the housing 242, and out of or behind the needle slot 258. As soon as the point 214 clears the needle slot 258, the locking arm 246 springs up (position D in FIG. 9), driven by the spring tension of the locking arm 246 in the housing 242. The needle point lock 240 can then be removed from the catheter 222, so that an intravenous line can be connected to the catheter 222. As the needle slot 258 has shifted upwardly, as shown in FIG. 9, the needle 212 can longer be moved forward out of the housing 242. Trying to push the needle 212 forward, as shown in FIG. 9, simply drives the point 214 into a solid section of the front leg 254 of the locking arm 246. The needle 212 also cannot be pulled out of the rear of the housing 242, as the upward shift of the locking arm 246, from position A in FIG. 8 to position D in FIG. 9, also pivots or moves the tab 256 at the back end of the locking arm 246 downwardly (from position C in FIG. 8, to position G in FIG. 9), allowing the wheel 264 to engage against the shaft 216 of the needle 212, at position F in FIG. 9. Once released by the movement of the tab 256, the wheel 264, driven by the spring 260, now engages the needle shaft 216 and the ramp 266, rather than the tab 256 and the ramp 266. The roughened or toothed surface of the wheel 264 grips the shaft 216 of the needle 212, and the ramp 266, preventing the needle 214 from moving rearwardly out of the housing 242.

The needle shaft 216 cannot move away from the wheel 264 biased into the shaft 216, as the shaft 216 is supported at the rear needle hole 270, and by the guide 286. Rearward movement of the needle shaft 216 causes the wheel 264 to move down the ramp 266 and into further and stronger engagement against the shaft 216. The roughened or toothed surface on the wheel 264 prevents slipping between the needle shaft 216 and wheel 264. As a result, the point 214 of the needle 212 is safely contained within the housing 242. The needle point lock 240 and needle assembly 202 (connected by the needle shaft 216) can then be safely discarded.

Since the catheter 222 cannot be accessed until the needle assembly 202 is withdrawn, (thereby automatically safely locking the needle point 214 within the needle point lock housing 242) the point locking safety feature does not rely on the attention of the user.

Thus, a novel safety catheter has been shown and described. Various modifications may of course be made without departing from the spirit and scope of the present invention.

I claim:

1. A safety catheter comprising:

a housing;

a needle having a point and a needle shaft, with the needle shaft extending entirely through the housing;

a catheter having a hub;

a catheter retainer on the housing, with the needle shaft extending through an opening in the catheter retainer; and locking means for preventing the point of the needle from being withdrawn from the housing.

2. The safety catheter of claim 1 further comprising a needle assembly having a housing cover adapted to fit over the needle point lock housing.

3. The safety catheter of claim 2 further comprising a flash back chamber on the housing cover, connecting to the needle.

4. The safety catheter of claim 1 wherein the catheter retainer comprises a locking arm having a hook extending outside of the needle point lock housing.

5. The safety catheter of claim 1 further comprising flanges on the hub of the catheter, and flange stops on the housing adjacent to the flanges.

6. A safety catheter comprising:

a needle assembly having a needle including a needle shaft and a needle point;

a needle point lock having a housing including: a front needle opening and a rear needle opening; a locking arm substantially within the housing, the locking arm having hook projecting outside of the housing, a front leg having a needle slot, and a rear tab; a ramp surface; a locking wheel; and a spring urging the wheel against the ramp surface; and a catheter having a hub with a flange, and with the hook engaging the flange;

the needle extending through the rear needle opening, the needle slot, the front needle opening and into the catheter, whereby the locking arm keeps the catheter attached to the housing until the needle is withdrawn into the housing and the needle slot moves out of alignment with needle preventing the needle from advancing forward, and the spring, wheel and ramp surface prevent the needle from being withdrawn rearwardly from the housing.

7. The safety catheter of claim 6 further comprising a flash back chamber and a housing cover on the needle assembly.

8. The safety catheter of claim 1 wherein the catheter retainer is biased radially away from the hub of the catheter.

9. The safety catheter of claim 8 wherein the catheter retainer comprises a spring element.

10. The safety catheter of claim 8 wherein the catheter retainer is held into an engaged position via the needle shaft extending through the catheter retainer, wherein the catheter retainer holds the catheter onto the housing.

11. The safety catheter of claim 1 wherein the opening in the catheter retainer is a hole or slot having a diameter or width to provide clearance for the needle shaft.

12. A safety catheter comprising:

a housing;

a needle extending entirely through the housing and a needle having a point and a shaft;

a catheter having a hub; and a locking arm in the housing having a hook extending outside of the housing, with the hook holding the hub of the catheter onto the housing.

13. The safety catheter of claim 12 further comprising an opening in the locking arm, with the needle shaft extending through the opening.

14. The safety catheter of claim 12 wherein the locking arm is substantially fixed in position with respect to the housing.

15. The safety catheter of claim 12 wherein the hook is automatically moved radially outwardly away from the hub of the catheter, by a distance sufficient to allow the catheter to be separated from the housing via movement in a direction parallel to the axis of the needle, when the needle point is withdrawn into the housing.

16. A safety catheter comprising:

a housing;

a needle having a point and extending entirely through the housing and the catheter;

a locking arm on the housing having a hook holding the catheter onto the housing;

means for biasing the locking arm away from the catheter;

means for holding the locking arm onto the catheter, until the needle point is withdrawn into the housing; and means for locking the needle point with the housing.

17. A safety catheter comprising:

a needle assembly having a needle including a needle shaft and a needle point;

a housing including a front needle opening and a rear needle opening;

a locking arm substantially within the housing, the locking arm having hook projecting outside of the housing, and a front leg having a needle arm opening;

a needle lock for preventing the needle point from being pulled out of the rear needle opening once the needle point is within the housing;

a catheter having a hub with a flange, and with the hook engaging the flange, the needle extending through the rear needle opening, the needle arm opening, the front needle opening and into the catheter;

whereby the locking arm keeps the catheter attached to the housing until the needle is withdrawn into the housing and the needle arm opening moves out of alignment with needle preventing the needle from advancing forward, and the needle lock prevents the needle from being withdrawn rearwardly from the housing.

18. A safety catheter comprising;

a housing;

a catheter having a hub;

a needle having a point, extending entirely through the housing and the catheter;

a spring biased locking arm in the housing;

a hook on the locking arm engaged onto the hub of the catheter against the spring bias of the locking arm and holding the hub onto the housing; and a needle lock in the housing for capturing the point of the needle within the housing.

19. A safety catheter comprising:

a needle point lock having a housing;

a needle assembly including a needle having a point and a needle shaft, with the needle shaft passing through the needle point lock housing;

a catheter having a hub;

catheter holding means for holding the catheter onto the needle point lock housing, until the needle point is drawn into the housing;

a ramp surface within the housing, a lock wheel on the ramp surface, and biasing means for urging the wheel into the ramp surface and towards the needle shaft.

* * * * *